United States Patent [19]

Stewart

[11] Patent Number: 4,656,004
[45] Date of Patent: Apr. 7, 1987

[54] MEDICAL HEAT EXCHANGE

[75] Inventor: Rodger L. Stewart, Lafayette, Colo.

[73] Assignee: Cobe Laboratories, Inc., Lakewood, Colo.

[21] Appl. No.: 735,332

[22] Filed: May 17, 1985

[51] Int. Cl.⁴ .................. A61M 1/14; A61M 1/34; F28D 7/04; F28F 1/10
[52] U.S. Cl. ..................... 422/46; 422/45; 128/DIG. 3; 165/163
[58] Field of Search ............ 422/45, 46; 128/DIG. 3; 165/160, 163

[56] References Cited

U.S. PATENT DOCUMENTS

| | | | |
|---|---|---|---|
| 4,065,264 | 12/1977 | Lewin | 165/163 X |
| 4,138,288 | 2/1979 | Lewin | 165/163 X |
| 4,160,801 | 7/1979 | Badolato et al. | 422/46 |
| 4,187,180 | 2/1980 | Joh | 210/321.3 X |
| 4,282,180 | 8/1981 | Raible | 422/46 |
| 4,424,190 | 1/1984 | Mather, III et al. | 422/46 |
| 4,440,723 | 4/1984 | Gordon | 422/46 X |

OTHER PUBLICATIONS

"William Harvey Introduces a New Geometry for Oxygenator Performance".

Primary Examiner—Barry S. Richman
Assistant Examiner—Lynn M. Kummert

[57] ABSTRACT

A medical device with a heat exchanger portion comprising a coiled, corrugated, flattened tube located in a flowpath provided between coaxial cylindrical walls, the tube having a cross sectional configuration including a length smaller in a first direction perpendicular to the axis of the inner and outer walls than in a second direction perpendicular to the first direction.

4 Claims, 2 Drawing Figures

MEDICAL HEAT EXCHANGE

FIELD OF THE INVENTION

This invention relates to heat exchange devices, as in medical devices such as oxygenators.

BACKGROUND OF THE INVENTION

A prior art heat exchanger particularly useful for oxygenators for blood is shown in Elgas et al. U.S. Pat. No. 4,451,562, the disclosures of which are hereby incorporated by reference herein.

Reduced priming volumes are known to be desirable, in particular in pediatric oxygenators.

SUMMARY OF THE INVENTION

I have discovered that if the corrugated tubing wound within a plastic annulus as in the above patent is flattened so that its thickness and the corresponding spacing of the walls of the annulus are reduced, with the reduction in distance being accomplished by decreasing the diameter of the outer wall inside diameter, heat transfer is significantly improved.

I have discovered also that if at least certain of the corrugations of the tubing are flattened, so that the radial height of the spaces defined between pairs of corrugations is reduced, this further improves heat transfer importantly.

Preferably, both discoveries are embodied, with consequent increases in heat transfer for permitting both reduction of priming volume and incurring less expense for materials in constructing the heat exchanger.

PREFERRED EMBODIMENT

I turn now to a description of the drawings and the structure and operation of a preferred embodiment.

DRAWINGS

STRUCTURE

Figure 1:
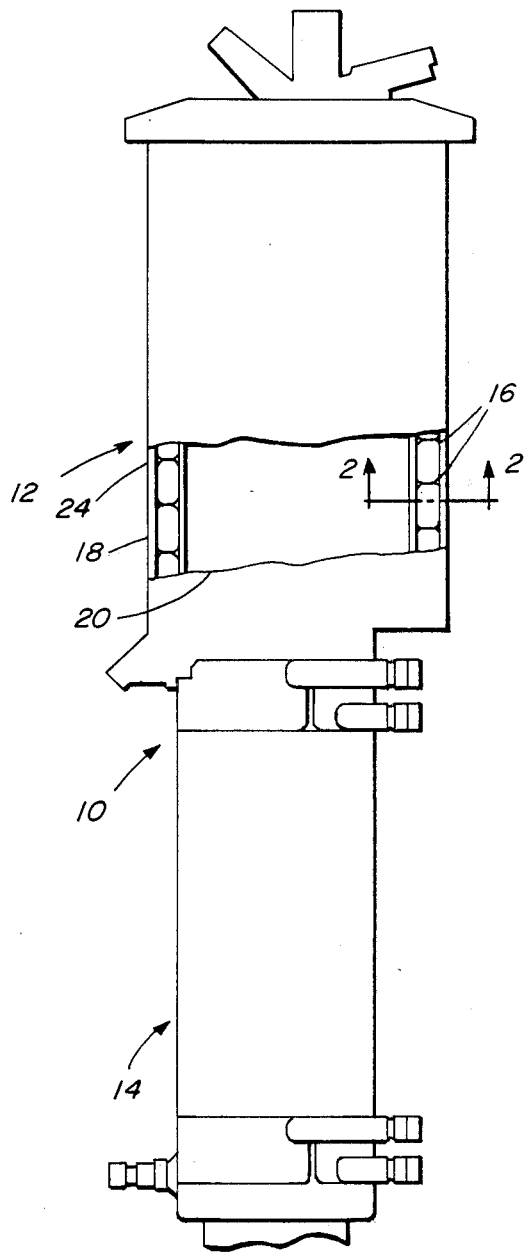
FIG. 1 is a side elevational view, partially in section, of said preferred embodiment.
Figure 2:
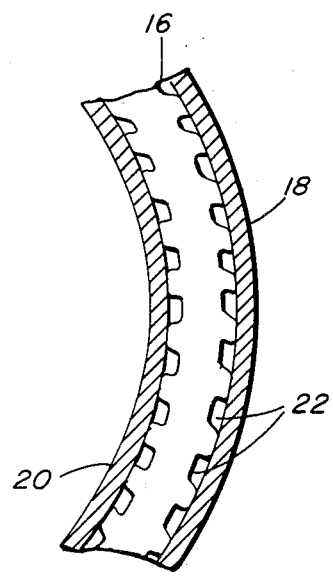
FIG. 2 is an enlarged sectional view taken at 2—2 thereof.

Referring now to FIG. 1, there is shown an oxygenator indicated generally at 10. Oxygenator 10 has reservoir portion 12 and oxygenator portion 14. Reservoir portion 12 includes a filter and a defoamer for air separation from venous blood introduced thereinto, as well as turns of heat exchanger tubing 16 wrapped between frustoconical plastic walls 18 and 20.

As shown in FIG. 1, tubing 16 has a height-to-width ratio of about 2 to 1, this tubing shape having been achieved by flattening tubing initially round in cross section using brake discs. A second change of configuration achieved in the flattening step just referred to was to reduce the depth of corrugations in the originally round and corrugated tubing.

Tubing 16 is formed of 304L stainless steel, with initial outside diameter of ¾ inch and root diameter of about ½ inch, the initial corrugations being defined, on a tubing longitudinal cross section, by alternating semicircles drawn alternatingly inwardly and outwardly from a line on said longitudinal cross section. The semicircles have radii that are half the distance between the outside and the root diameters. Initial corrugation depth was about ⅛ inch.

After deformation in the brake die, cross sectional outer tubing dimensions are 0.45 by about 0.950 inches, and corrugation 22 depth is about 0.070 inch.

OPERATION

Blood enters the heat exchanger portion of reservoir portion 12 through the annulus 24 between walls 18 and 20, and flows downward past the turns of the heat exchanger tubing 16.

Because of the flattened shape of tubing 16, the area left for blood flow, between the outer surface thereof and the surfaces of walls 18 and 20, is greatly reduced, wholly aside from corrugation depth. This means that blood flow velocity must increase in order to obtain the same blood flow volume, and also that laminar boundary layers in a heat flow direction become thinner, both conducing, through increased laminar mixing and otherwise, to improved heat transfer.

A further factor reducing effective overall cross sectional area of blood flow is that by virtue of the flattening the overall outside diameter of the tubing helix 16, and therefore its average diameter, is reduced.

At the same time, because of flattening of the corrugations 22, both the volume and the thickness of a given portion thereof is reduced, again further improving heat transfer, because of both laminar mixing and thickness effects.

In consequence of all this, smaller amounts of blood are required for priming, and material of construction can be saved because the size of the heat exchange portion needed can be reduced.

Other embodiments within the following claims will occur to those skilled in the art.

I claim:

1. A heat exchanger comprising
   a housing having a continuous outer housing wall,
   a coaxial continuous inner housing wall having the same shape as said outer housing wall and spaced inward of said outer housing wall to define a constant width axial flowpath chamber therebetween, and
   a conduit wrapped around said inner housing wall in said flowpath chamber between said outer housing wall and said inner housing wall,
   said conduit having a cross sectional configuration including a length smaller in a first direction transverse to said inner and outer walls than in a second longitudinal direction relative to said inner and outer walls,
   said conduit including corrugations extending generally in said axial flowpath direction.

2. The heat exchanger of claim 1 in which said corrugations have a configuration such that they have generally flat surfaces at portions adjacent to said inner and outer walls.

3. The heat exchanger of claim 2 in which said conduit is tubing flattened to produce both said cross sectional and corrugations configurations.

4. In oxygenation apparatus comprising an oxygenator and a heat exchanger having a housing having a continuous outer housing wall, a coaxial continuous inner housing wall having the same shape as said outer housing wall and spaced inward of said outer housing wall to define a constant width axial flowpath chamber therebetween, and a conduit wrapped around said inner housing wall in said flowpath chamber between said outer housing wall and said inner housing wall, said conduit including corrugations extending generally in said axial flowpath direction, wherein the improvement comprises said conduit having a cross sectional configuration including a length smaller in a first direction transverse to said inner and outer walls than in a second longitudinal direction relative to said inner and outer walls.

* * * * *